United States Patent
Dassanayake et al.

(10) Patent No.: US 6,962,693 B2
(45) Date of Patent: Nov. 8, 2005

(54) ALKYLPOLYPROPYLENEOXIDE AMIDOTRIAMINES AND METHOD OF USING SAME

(75) Inventors: Nissanke L. Dassanayake, Arlington, TX (US); Ronald L. Schlitzer, Fort Worth, TX (US)

(73) Assignee: Alcon, Inc., Hunenberg (CH)

( * ) Notice: Subject to any disclaimer, the term of this patent is extended or adjusted under 35 U.S.C. 154(b) by 75 days.

(21) Appl. No.: 11/000,230

(22) Filed: Nov. 30, 2004

(65) Prior Publication Data

US 2005/0136029 A1    Jun. 23, 2005

Related U.S. Application Data

(60) Provisional application No. 60/531,469, filed on Dec. 19, 2003.

(51) Int. Cl.[7] .................. A61K 31/075; A61K 31/131; A61K 31/16
(52) U.S. Cl. .................. 424/78.04; 514/839; 514/840; 564/123; 564/192; 528/332; 510/112; 510/501; 510/382; 510/383
(58) Field of Search .................. 510/112, 501, 382, 510/383; 424/78.04; 514/839, 840; 564/123, 564/192; 528/332; 422/28

(56) References Cited

U.S. PATENT DOCUMENTS

| | | | |
|---|---|---|---|
| 4,119,668 A | 10/1978 | Diana et al. | |
| 4,525,346 A | 6/1985 | Stark | |
| 4,537,746 A | 8/1985 | Ogunbiyi et al. | |
| 5,573,726 A * | 11/1996 | Dassanayake et al. | ........ 422/28 |
| 5,627,214 A | 5/1997 | Schafer et al. | |
| 5,631,005 A | 5/1997 | Dassanayake et al. | |
| 5,965,088 A * | 10/1999 | Lever et al. | .................. 422/28 |

* cited by examiner

*Primary Examiner*—Gregory R. Del Cotto
(74) *Attorney, Agent, or Firm*—Gregg C. Browh

(57) ABSTRACT

Alkylpolypropyleneoxide amidotriamines having antimicrobial activity are described. The compounds are useful as antimicrobial preservatives in various types of pharmaceutical compositions. Ophthalmic compositions containing these compounds as disinfecting agents or preservatives are also described.

4 Claims, No Drawings

ALKYLPOLYPROPYLENEOXIDE AMIDOTRIAMINES AND METHOD OF USING SAME

CLAIM FOR PRIORITY

This application claims priority from U.S. Patent Application Ser. No. 60/531,469, filed Dec. 19, 2003.

BACKGROUND OF INVENTION

The present invention relates to the field of ophthalmology. More specifically, the invention is directed to compositions and methods for disinfecting contact lenses, and to the preservation of various types of pharmaceutical compositions, particularly ophthalmic, otic and nasal pharmaceutical compositions and compositions for treating contact lenses.

Contact lenses are exposed to a broad spectrum of microbes during normal wear and become soiled relatively quickly. Routine cleaning and disinfecting of the lenses are therefore required. Although the frequency of cleaning and disinfecting may vary somewhat among different types of lenses and lens care regimens, daily cleaning and disinfecting is normally required. Failure to clean and disinfect the lens properly can lead to a multitude of problems ranging from mere discomfort when the lenses are being worn to serious ocular infections. Ocular infections caused by particularly virulent microbes, such as *Pseudomonas aeruginosa*, can lead to loss of the infected eye(s) if left untreated, or if allowed to reach an advanced stage before treatment is initiated. It is therefore extremely important that patients disinfect their contact lenses in accordance with the regimen prescribed by their optometrist or ophthalmologist.

Unfortunately, patients frequently fail to follow the prescribed regimens. Many patients find regimens to be difficult to understand and/or complicated, and as a result do not comply with one or more aspects of the regimen. Other patients may have a negative experience with the regimen, such as ocular discomfort attributable to the disinfecting agent, and as a result do not routinely disinfect their lenses or otherwise stray from the prescribed regimen. In either case, the risk of ocular infections is exacerbated.

The use of amidoamines, quaternary ammonium compounds, and biguanides as disinfecting agents is well known. The following U.S. patents may be referenced for further background regarding the use of such compounds in the ophthalmic field: U.S. Pat. No. 5,631,005; U.S. Pat. No. 4,525,346; and U.S. Pat. No. 4,537,746.

The inclusion of long chain alkyl groups in amidoamine and quaternary ammonium compounds generally increases the antimicrobial activity of these compounds. However, as the chain length is increased, the solubility of the compounds in water decreases. The reduction in solubility negates the improved antimicrobial activity resulting from the increased chain length.

Solubility and associated antimicrobial activity may be further affected by buffered solutions, such as those typically used in contact lens disinfection. There is, therefore, a need for a means of enhancing the activity of antimicrobial agents by increasing alkyl chain length without reducing the solubility of the agents.

SUMMARY OF THE INVENTION

The present invention has resolved the above-cited problem by utilizing a combination of alkyl and polypropylene oxide groups to render known hydrophilic antimicrobial agents more hydrophobic, without reducing the solubility of the agents. The increased hydrophobicity provides the compounds of the present invention with enhanced antimicrobial activity. The excellent antimicrobial activity and aqueous solubility of the compounds of the present invention make the compounds particularly suitable as antimicrobial preservative agents in aqueous pharmaceutical compositions, particularly ophthalmic, otic and nasal compositions, as well as contact lens disinfecting solutions and other products used to treat contact lenses.

DETAILED DESCRIPTION OF THE INVENTION

The structural formula of the compounds of the present invention is as follows:

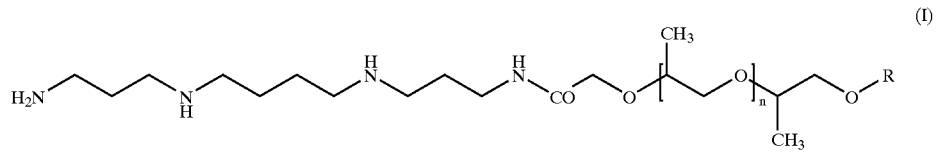

(I)

wherein:

R is $C_6$ to $C_{18}$ alkyl; and n is a whole number of from 1 to 100.

The alkyl groups can be branched or straight, saturated or unsaturated. The alkyl groups may also contain one or more aryl groups or heteroatoms (e.g., oxygen). The compounds of the present invention also include pharmaceutically acceptable salts of the foregoing compounds.

The preferred compounds of the formula (I) above are those wherein n is 6 to 12 and R is a $C_2$—$C_6$ alkyl group.

The most preferred compounds are identified in the following table:

| Compound Number | Polypropyleneoxide Units Average Number (n) | Carbon Content of Alkyl Group (R) |
|---|---|---|
| AL-12184 | 8 | 6 |
| AL-9201 | 12 | 8 |
| AL-12223 | 12 | 10 |
| AL-13107 | 6 | 10 |
| AL-12246 | 12 | 12 |
| AL-12826 | 6 | 12 |
| AL-12413 | 6 | 14 |
| AL-12231 | 12 | 14 |
| AL-9548 | 16 | 8 |
| AL-9552 | 33 | 8 |

| Compound Number | Polypropyleneoxide Units Average Number (n) | Carbon Content of Alkyl Group (R) |
|---|---|---|
| AL-9577 | 50 | 8 |
| AL-9599 | 68 | 8 |
| AL-12414 | 16 | 14 |
| AL-12431 | 33 | 14 |
| AL-12432 | 50 | 14 |
| AL-12475 | 68 | 14 |
| AL-12960 | 6 | 16 |
| AL-12961 | 12 | 16 |
| AL-13093 | 6 | 18 |
| AL-13095 | 12 | 18 |

The alkylpolypropyleneoxide amidotriamines of formula (I) may be synthesized as follows: First, polypropylene glycol is alkylated by adding a halogenated alkane, (e.g., 1-bromooctane) to a mixture of polypropylene glycol and potassium hydroxide, to yield an alkoxylated polypropylene alcohol. The resulting polypropylene alcohol is then further alkylated by adding allyl bromide to a mixture of the polypropylene alcohol and potassium hydroxide to yield a dialkoxylated polypropylene. Then one of the alkoxy groups of the dialkoxylated polypropylene is esterified to yield a methyl ester by passing ozone through a mixture of the dialkoxylated polypropylene, dichloromethane, and methanolic sodium hydroxide. The resulting methyl ester moiety is aminated by adding the methyl ester to a mixture of spermine and trimethylaluminum in hexane, to yield an alkylpolypropyleneoxide amidotriamine of formula (I).

A more detailed illustration of the process for preparing the alkylpolypropylene oxide amidotriamines of the present invention is provided below:

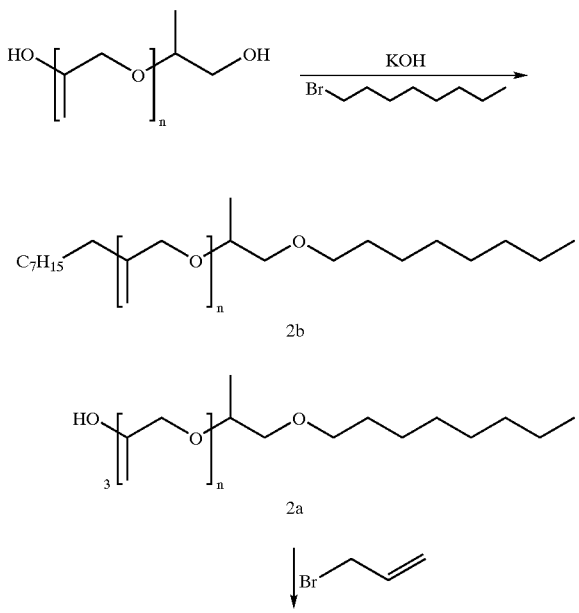

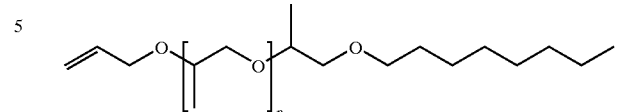

To a mixture of polypropyleneglycol (Aldrich Cat. No 20,233-9, Ave MW 2,000) (16.0 g, 8.0 mmol) and 85% KOH powder (3.21 g, 48.6 mmol) is added dropwise 1-bromooctane (3.0 ml, 17.2 mmol). After the reaction mixture is stirred at room temperature for 44 hours, it is diluted with ether and filtered through filter paper. The combined filtrates are concentrated under reduced pressure and purified by $SiO_2$ column chromatography using 1:4 to 1:1 EtOAc-hexane, followed by EtOAc, as gradient eluents, affording the desired alcohol 2a (8.53 g, 51%) and the dialkylated side-product 2b (4.38 g, 25%).

The second alkylation is then carried out by slow addition of allyl bromide (1.2 ml, 13.7 mmol) to a mixture of the alcohol 2a (5.81 g, 2.75 mmol) and 85% KOH powder (2.19 g, 33.2 mmol). The mixture is stirred at room temperature for 40 hours, then diluted with ether, and filtered through a pad of Celite. The filtrate is concentrated under reduced pressure and purified by $SiO_2$ column chromatography (eluting with 1:2 to 1:1 EtOAc-hexane) to give the ether 3 (5.92 g, 100%).

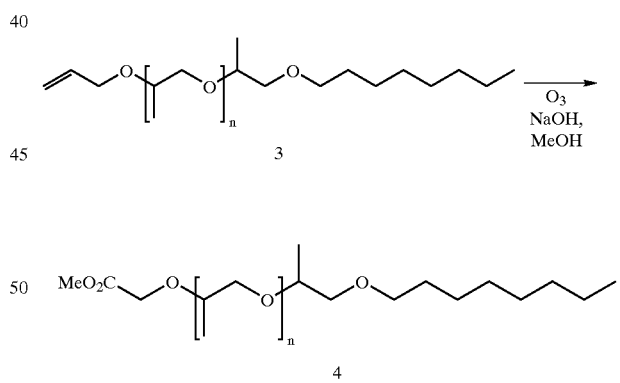

The ether 3 (2.68 g, 1.25 mmol) is dissolved in a mixture of $CH_2Cl_2$ (40 ml) and 1.0M methanolic NaOH (6.5 ml). Ozone is passed through the solution, which is cooled to −78° C. The initially yellow reaction mixture turns pale blue and white precipitates are formed (over 40 minutes). The mixture is concentrated in vacuo to dryness and EtOAc is added. The EtOAc extract is filtered through a pad of Celite, dried over $Na_2SO_4$, and concentrated in vacuo. Purification by silica gel column chromatography using 1:2 EtOAc-hexane provides the methyl ester 4 (1.80 g, 66%).

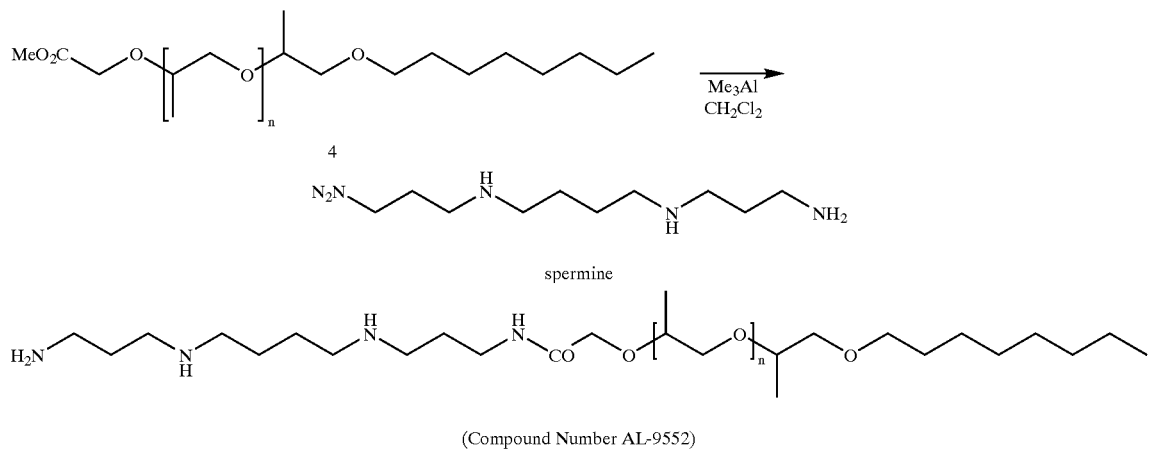

(Compound Number AL-9552)

To a solution of spermine (240 mg, 1.2 mmol) in anhydrous $CH_2Cl_2$ (8 ml) is added dropwise a 2.0 M solution of trimethylaluminum in hexane (0.6 ml). After the mixture is stirred at room temperature for 15 min, a solution of the methyl ester 4 (0.42 g, 0.2 mmol) in $CH_2Cl_2$ (8 ml) is added. The resulting mixture is heated at reflux for 2 hours, and quenched with addition of saturated aqueous $NaHCO_3$ solution. The mixture is dried over $Na_2SO_4$, filtered, and concentrated in vacuo. Purification by silica gel column chromatography (elution with EtOAc, followed by 16:5:1 $CHCl_3$—MeOH—$NH_4OH$) affords the target compound as a slightly yellow oil (285 mg, 64%).

The compounds of the present invention can be used individually, in combination with one or more other compounds of the present invention, or in combination with other disinfectants or preservatives. The compounds may, for example, be used in combination with the polyquaternium-1 or other polymeric quaternary ammonium compounds described in U.S. Pat. No. 4,525,346; the entire contents of the '346 patent are hereby incorporated in the present specification by reference.

The polymeric quaternary ammonium compounds described in the '346 patent are useful in disinfecting contact lenses and preserving ophthalmic compositions. The most preferred polymeric quaternary ammonium compound is polyquaternium-1, which is also known as Onamer-M™ (trademark of Onyx Chemical Company) and Polyquad® (registered trademark of Alcon Laboratories, Inc.). The amount of polyquaternium-1 utilized will generally be in the range of from about 0.00005 to about 0.01 percent by weight, based on the total weight/volume ("w/v %").

The amount of each compound used will depend on the purpose of the use, e.g., disinfection of contact lenses or preservation of compositions from contamination, and the absence or inclusion of other antimicrobial agents. The concentrations determined to be necessary for the above-stated purposes can be functionally described as "an amount effective to disinfect" and "an amount effective to preserve" or variations thereof. The concentrations used for disinfection will generally be in the range of from about 0.00005 to about 0.1 w/v %. The concentrations used for antimicrobial preservation will generally be in the range of from about 0.00001 to about 0.05 w/v %.

The compounds of the present invention may be included in various types of pharmaceutical compositions as antimicrobial preservatives, so as to prevent microbial contamination of the compositions. The compounds are particularly useful as antimicrobial preservatives in ophthalmic, otic and nasal compositions. The types of ophthalmic compositions which may be preserved by the compounds of the present invention include: ophthalmic pharmaceutical compositions, such as topical compositions used in the treatment of glaucoma, infections, allergies or inflammation; compositions for treating contact lenses, such as cleaning products and products for enhancing the ocular comfort of patients wearing contact lenses; and various other types of compositions, such as ocular lubricating products, artificial tears, astringents, and so on. The compositions may be aqueous or nonaqueous, but will generally be aqueous.

As will be appreciated by those skilled in the art, the compositions of the present invention may contain a wide variety of ingredients, such as tonicity agents (e.g., sodium chloride or mannitol), surfactants, viscosity adjusting agents (e.g., hydroxypropyl methyl cellulose and other cellulose derivatives), and buffering agents (e.g., borates, citrates, phosphates and carbonates). The present invention is not limited with respect to the types of ophthalmic compositions in which the compounds of the present invention may be contained as preservatives. In fact, as already noted above, the compatibility of the compounds of the present invention with other ingredients of ophthalmic compositions, such as inorganic ions, polymers and surfactants, is a distinct advantage of the present invention, relative to antimicrobial agents previously utilized in the ophthalmic field.

The contact lens disinfecting compositions of the present invention will preferably be formulated as aqueous solutions, but may also be formulated as nonaqueous solutions, as well as suspensions, gels, and so on. The compositions may contain a variety of tonicity agents, surfactants, viscosity adjusting agents and buffering agents, as described above. The chemical compatibility of the compounds of formula (I) with such agents is also a significant advantage with respect to the use of these compounds in the contact lens disinfecting compositions of the present invention.

The above-described compositions may be used to disinfect contact lenses in accordance with processes known to those skilled in the art. More specifically, the lenses will first be removed from the eyes of the patients, and then will be immersed in compositions for a time sufficient to disinfect the lenses. This immersion will typically be accomplished by means of soaking the lenses in a solution overnight (i.e., approximately six to eight hours). The lenses will then be rinsed and placed in the eye. Prior to immersion in the disinfecting compositions, the lenses will preferably also be cleaned and rinsed.

The compounds of formula (I) also have surface active properties. As a result of these properties, the compounds are also useful in cleaning contact lenses. More specifically, the surfactant properties of the compounds facilitate the removal of deposits typically accumulated on contact lenses when worn by human patients. These deposits vary from patient to patient, but will typically include proteins, lipids, polysaccharides and mixtures thereof, as well as various other soils which may accumulate on the lenses during normal wear and handling. The compounds will exhibit some cleaning effect even at the relatively low concentrations required for purposes of preserving ophthalmic compositions or disinfecting contact lenses. This cleaning effect is therefore useful as a supplement to the effect of other cleaning agents which may be contained in the compositions, such anionic or nonionic surfactants. Moreover, when used at a concentration of 0.01 w/v % or higher, the compounds exhibit a more pronounced cleaning effect.

The manner in which the cleaning effect of the compounds of the present invention is utilized will depend on the type of contact lens being treated, the severity and type of the deposits on the lenses, and the overall treatment regimen used by the patient. The selection of other components for inclusion in the contact lens cleaning compositions of the present invention will also depend on these factors. The cleaning compositions will generally contain one or more of the compounds of the present invention in an amount of at least 0.01 w/v %, and preferably from about 0.01 to 1.0 w/v %.

The above-described compositions may be used to clean contact lenses in accordance with known processes. For example, the lenses, after first being removed from the eye and preferably also rinsed, may be lightly rubbed with a small amount of the compositions between the fingers, or may be immersed in a somewhat larger volume of the compositions and then allowed to soak. The lenses are then rinsed and disinfected before being replaced in the eyes of the patients.

All of the above-described compositions will be formulated so as to be compatible with the eye and/or contact lenses to be treated with the compositions. As will be appreciated by those skilled in the art, the ophthalmic compositions intended for direct application to the eye will be formulated so as to have a pH and tonicity, which are compatible with the eye. This will normally require a buffer to maintain the pH of the composition at or near physiologic pH (i.e., 7.4) and may require a tonicity agent to bring the osmolality of the composition near to 300 mOs/kg. The formulation of compositions for disinfecting and/or cleaning contact lenses will involve similar considerations, as well as considerations relating to the physical effect of the compositions on contact lens materials and the potential for binding or absorption of the components of the composition by the lens.

The compositions and methods of the present invention may be used in conjunction with various types of contact lenses, including both lenses generally classified as "hard" and lenses generally classified as "soft".

EXAMPLE 1

The following formulation may be utilized as a contact lens disinfecting solution. The formulation would contain one or more compounds of formula (I) as a disinfectant.

| Component | Formulation Numbers/Concentrations | |
|---|---|---|
| | FID 93407 | FID 84509 |
| Sorbitol | 1.2% | — |
| Sodium Citrate | 0.6% | — |
| Boric Acid | | 0.18% |
| Sodium chloride | 0.1% | 0.49% |
| Tetronic 1304 | 0.1% | — |
| EDTA | 0.05% | 0.05% |
| AMP (95%) | 0.45% | — |
| pH | 7.8 | 7.0 |

EXAMPLE 2

The tests described below were conducted to evaluate the antimicrobial activity of the compounds and compositions of the present invention. To perform these tests, the bacteria *Serratia marcescens* ATCC 13880 and *Staphylococcus aureus* ATCC 6538 were cultured on soybean casein digest agar (SCDA) slants. The yeast *Candida albicans* ATCC 10231 was cultured on Sabouraud Dextrose Agar slants. Surface growth of the three microorganisms was harvested with phosphate buffered saline containing Polysorbate 80. The microbial suspensions were adjusted spectrophotometrically to a concentration of approximately $1.0 \times 10^8$ colony forming units/mL (CFU/mL).

Antimicrobial compounds were prepared at target concentrations in selected vehicles. Ten mL of test solution was inoculated with 0.1 mL of the appropriate microbial suspension so that the test solution contained approximately $1.0 \times 10^6$ CFU/mL. The tubes were thoroughly mixed and kept at room temperature during the test.

At six and 24 hours after test solution inoculation, a 1.0 mL aliquot from each test sample and for each challenge organism was transferred to 9.0 mL Dey Engley Neutralizing Broth blanks. The samples were serially diluted in the neutralizing broth and pour plates were prepared from appropriate dilutions with SCDA containing neutralizers. Petri plates were incubated for 48–72 hours and the number of survivors visible as discrete colony forming units were determined according to standard microbiological methods.

The results of the tests are provided in Tables 1–4 below:

TABLE 1

Antimicrobial Activity of Alkyl PPO Amidotriamine Compounds ($8.8 \times 10^{-5}$ M) in FID 84509

$Log_{10}$ Reduction of Survivors

| Microorganism | Time (hrs) | AL-12184 $C^a_8n_6{}^b$ | AL-9201 $C_8n_{12}$ | AL-13107 $C_{10}n_6$ | AL-12223 $C_{10}n_{12}$ | AL-12826 $C_{12}n_6$ | AL-12246 $C_{12}n_{12}$ | AL-12413 $C_{14}n_6$ | AL-12231 $C_{14}n_{12}$ |
|---|---|---|---|---|---|---|---|---|---|
| C. albicans | 6 | 0.0 | 0.0 | 2.3 | 3.7 | 2.2 | 2.7 | 2.0 | 0.2 |
| | 24 | 0.3 | 0.4 | 3.6 | 5.0 | 5.2 | 5.0 | 5.0 | 1.0 |
| S. marcescens | 6 | 3.0 | 5.4 | 3.4 | 6.1 | 4.0 | 5.4 | 5.4 | 3.2 |
| | 24 | 3.7 | 5.4 | 4.7 | 6.1 | 5.5 | 5.4 | 6.1 | 4.4 |
| S. aureus | 6 | 2.9 | 3.9 | 2.7 | 4.4 | 2.4 | 3.7 | 3.9 | 3.7 |
| | 24 | 3.8 | 6.0$^c$ | 3.9 | 5.3 | 2.6 | 5.3 | 5.3 | 5.3 |

6006:047, 049, 050, 052, 063, 074

$^a$Alkyl chain
$^b$average number PPO repeating units
$^c$Underlined number indicates no survivors (<10 CFU/mL) recovered

TABLE 2

Antimicrobial Activity of Alkyl PPO Amidotriamine Compounds ($8.8 \times 10^{-6}$ M) in FID 84509

$Log_{10}$ Reduction of Survivors

| Microorganism | Time (hrs) | AL-12184 $C^a_8n_6{}^b$ | AL-9201 $C_8n_{12}$ | AL-13107 $C_{10}n_6$ | AL-12223 $C_{10}n_{12}$ | AL-12826 $C_{12}n_6$ | AL-12246 $C_{12}n_{12}$ | AL-12413 $C_{14}n_6$ | AL-12231 $C_{14}n_{12}$ |
|---|---|---|---|---|---|---|---|---|---|
| C. albicans | 6 | −0.3 | −0.3 | −0.1 | −0.3 | 0.4 | 0.1 | 1.3 | 0.2 |
| | 24 | −0.2 | −0.2 | 0.0 | 0.0 | 0.6 | 0.9 | 2.4 | 0.9 |
| S. marcescens | 6 | 0.5 | 2.3 | 2.2 | 3.3 | 2.8 | 2.6 | 2.6 | 2.6 |
| | 24 | 0.8 | 3.1 | 2.5 | 3.5 | 3.6 | 3.5 | 3.3 | 3.4 |
| S. aureus | 6 | −0.2 | 0.7 | 0.1 | 1.8 | 3.9 | 2.4 | 1.8 | 2.0 |
| | 24 | 0.7 | 2.8 | 1.9 | 2.7 | 5.2 | 2.8 | 2.5 | 2.4 |

6006:047, 049, 050, 052, 063, 078

$^a$Alkyl chain
$^b$average number PPO repeating units
$^c$Underlined number indicates no survivors (<10 CFU/mL) recover

TABLE 3

Disinfection Efficacy of 0.0005% Alkyl PPO Amidotriamine Compounds in Water $Log_{10}$ Reduction of Survivors

| Microorganism | Time (hrs) | AL-12246 $C_{12}{}^a n_{12}{}^b$ | AL-12413 $C_{14}n_6$ | AL-12826 $C_{12}n_6$ |
|---|---|---|---|---|
| C. albicans | 6 | 1.4 | 1.9 | 1.7 |
| | 24 | 1.0 | 2.9 | 2.1 |
| S. marcescens | 6 | 6.2$^c$ | 3.5 | 6.2 |
| | 24 | 6.2 | 3.8 | 6.2 |
| S. aureus | 6 | 6.1 | 2.8 | 6.1 |
| | 24 | 6.1 | 2.5 | 6.1 |

6006:017, 092

$^a$Alkyl chain
$^b$average number of PPO repeating units
$^c$Underlined number indicates no survivors (<10 CFU/mL) recovered

TABLE 4

Disinfection Efficacy of 0.001% Alkyl PPO Amidotriamine Compounds

| | | \multicolumn{3}{c}{Log$_{10}$ Reduction of Survivors} | | | |
| --- | --- | --- | --- | --- | --- | --- | --- |
| | | ID 90081 Vehicle | | | ID 93407 Vehicle | | |
| Microorganism | Time (hrs) | AL-12246 $C_{12}{}^a n_{12}{}^b$ 98066$^c$ | AL-12413 $C_{14} n_6$ 98064 | AL-12826 $C_{12} n_6$ 98062 | AL-12246 $C_{12} n_{12}$ 98065 | AL-12413 $C_{14} n_6$ 98063 | AL-12826 $C_{12} n_6$ 98061 |
| C. albicans | 6 | 1.1 | 2.5 | 2.6 | 0.4 | 0.9 | 1.2 |
| | 24 | 1.8 | 2.9 | 3.4 | 0.1 | 1.7 | 2.5 |
| S. marcescens | 6 | <u>6.1</u>$^d$ | <u>6.1</u> | <u>6.1</u> | 0.3 | 5.4 | <u>6.1</u> |
| | 24 | <u>6.1</u> | <u>6.1</u> | <u>6.1</u> | 2.3 | <u>6.1</u> | <u>6.1</u> |
| S. aureus | 6 | 4.4 | 4.7 | 5.6 | 0.1 | 4.1 | 4.2 |
| | 24 | <u>6.3</u> | <u>6.3</u> | <u>6.3</u> | 0.1 | <u>6.3</u> | 5.3 |
| | | | | | | | 6033:100 |
| | | | | | | | 6035:086 |

$^a$Alkyl chain
$^b$average number of PPO repeating units
$^c$Disinfection Research test article number
$^d$Underlined number indicates no survivors (<10 CFU/mL) recovered

EXAMPLE 3

The test procedures described in Example 2 above were used to evaluate the amidotriamine compounds AL-9201, AL-9548, AL-9552, and AL-9577 at a concentration of 0.001% in water and FID 84509. The results are presented in Tables 5 and 6, below:

TABLE 5

Disinfection Efficacy of 0.001% Amidotriamine Compounds in Water

| | Time | \multicolumn{4}{c}{Log$_{10}$ Reduction of Survivors} | | | |
| --- | --- | --- | --- | --- | --- |
| Microorganism | (hrs) | AL-9201 | AL-9548 | AL-9552 | AL-9577 |
| C. albicans | 6 | 4.1 | 2.4 | 0.4 | 0.1 |
| | 24 | 5.9$^a$ | <u>5.9</u> | 1.6 | 0.3 |
| S. marcescens | 6 | 4.3 | 4.3 | <u>6.1</u> | 3.4 |
| | 24 | 5.4 | 4.7 | 3.0 | 4.2 |
| S. aureus | 6 | 3.2 | 3.3 | 2.4 | 2.1 |
| | 24 | 2.2 | 5.2 | 5.2 | 3.6 |

$^a$Underlined number indicates no survivors (<10 cfu/ml) recovered

TABLE 6

Disinfection Efficacy of 0.001% Amidotriamine Compounds in FID 84509

| | Time | \multicolumn{4}{c}{Log$_{10}$ Reduction of Survivors} | | | |
| --- | --- | --- | --- | --- | --- |
| Microorganisms | (hrs) | AL-9201 | AL-9548 | AL-9552 | AL-9577 |
| C. albicans | 6 | 0.1 | 0.1 | 0.0 | 0.0 |
| | 24 | 0.1 | 0.1 | 0.2 | 0.0 |
| S. marcescens | 6 | 3.2 | 2.5 | 3.1 | 2.2 |
| | 24 | 3.8 | 3.6 | 3.2 | 3.2 |
| S. aureus | 6 | 0.0 | 0.4 | 2.0 | 0.0 |
| | 24 | 2.7 | 2.9 | 2.8 | 0.0 |

The results further demonstrate the strong antimicrobial activity and salt sensitivity of these compounds.

EXAMPLE 4

The test procedures described above were utilized for six amidotriamine compounds containing different molecular weights of polyoxypropylene. The compounds were evaluated in water at a concentration of 0.001 w/v %, and in FID 84509 at a concentration of 0.005 w/v %. The results are presented in Tables 7 and 8, below:

TABLE 7

Disinfection Efficacy of 0.001% Amidotriamine Compounds in Water$^a$

| | Time | \multicolumn{6}{c}{Log$_{10}$ Reduction of Survivors} | | | | | |
| --- | --- | --- | --- | --- | --- | --- | --- |
| Microorganism | (hrs) | AL12184 (7.3)$^b$ [6]$^c$ | AL9201 (7.1) [12] | AL9548 (6.9) [16] | AL9552 (6.8) [33] | AL9577 (6.5) [50] | AL9599 (6.5) [68], |
| C. albicans | 6 | 3.4 | 3.0 | 3.2 | 0.7 | 0.3 | 0.1 |
| | 24 | 3.7 | 3.6 | 3.6 | 1.4 | 0.3 | 0.1 |
| S. marcescens | 6 | 3.7 | 2.9 | 3.8 | 4.2 | 2.2 | 2.0 |
| | 24 | 4.9 | 2.9 | <u>6.2</u>$^d$ | 3.4 | 3.0 | 2.7 |

TABLE 7-continued

Disinfection Efficacy of 0.001% Amidotriamine Compounds in Water[a]

| | | Log$_{10}$ Reduction of Survivors | | | | | |
|---|---|---|---|---|---|---|---|
| Microorganism | Time (hrs) | AL12184 (7.3)[b] [6][c] | AL9201 (7.1) [12] | AL9548 (6.9) [16] | AL9552 (6.8) [33] | AL9577 (6.5) [50] | AL9599 (6.5) [68], |
| S. aureus | 6 | 2.9 | 3.2 | 3.0 | 3.8 | 2.3 | 1.6 |
| | 24 | 3.0 | 4.1 | 4.5 | 4.9 | 4.2 | 3.0 |

[a]Not sterile filtered
[b]Formulation pH
[c]Number of PPO units
[d]Underlined number indicates no survivors (<10 cfu/ml) recovered

TABLE 8

Disinfection Activity of 0.005% Amidotriamine Compounds in FID 84509[a,b]

| | | Log$_{10}$ Reduction of Survivors | | | | | |
|---|---|---|---|---|---|---|---|
| Microorganisms | Time (hrs) | AL12184 [6] | AL9201 [12][c] | AL9548 [16] | AL9552 [33] | AL9577 [50] | AL9599 [68] |
| C. albicans | 6 | −0.2 | 0.0 | 0.1 | 0.1 | 0.0 | 0.0 |
| | 24 | 0.4 | 0.4 | 0.9 | 0.7 | 0.1 | 0.0 |
| S. marcescens | 6 | 1.7 | 4.0 | 2.9 | 3.3 | 2.4 | 1.2 |
| | 24 | 2.3 | 4.4 | 5.4 | 2.3 | 2.7 | 2.8 |
| S. aureus | 6 | 3.4 | 3.2 | 4.1 | 1.8 | −0.1 | −0.1 |
| | 24 | 4.5 | 3.7 | 4.7 | 5.0 | 1.7 | 0.1 |

[a]Not sterile filtered
[b]Formulation pH 7.0
[c]Number of PPO units

These results show that increasing the number of PPO groups will lower the antimicrobial activity of the compound. This is true in water and buffered solution.

EXAMPLE 5

The test procedures described above were utilized to evaluate the amidotriamine compounds AL-9201 and AL-12223 in water and FID 84509 at a concentration of 0.001 w/v %. The results are presented in Table 9, below:

TABLE 9

Disinfection Activity of 0.001% Alkyl/PPO Amidotriamine Compounds

| | | Log$_{10}$ Reduction of Survivors | | | |
|---|---|---|---|---|---|
| | Time | Water | | FID 84509 | |
| Microorganisms | (hrs) | AL9201 | AL12223 | AL9201 | AL12223 |
| C. albicans | 6 | 2.3 | 3.8 | 0.3 | 0.4 |
| | 24 | 2.6 | 6.0 | 0.2 | 1.1 |
| S. marcescens | 6 | 2.7 | 4.8 | 2.4 | 2.5 |
| | 24 | 3.5 | 6.0[a] | 3.4 | 3.5 |

TABLE 9-continued

Disinfection Activity of 0.001% Alkyl/PPO Amidotriamine Compounds

| | | Log$_{10}$ Reduction of Survivors | | | |
|---|---|---|---|---|---|
| | Time | Water | | FID 84509 | |
| Microorganisms | (hrs) | AL9201 | AL12223 | AL9201 | AL12223 |
| S. aureus | 6 | 2.6 | 2.2 | 0.3 | 2.7 |
| | 24 | 4.3 | 4.2 | 3.4 | 3.6 |

[a]Underlined number indicates no survivors (<10 cfu/ml) recovered

The results again show the strong antimicrobial activity of these types of compounds in water as well as their sensitivity to salts.

EXAMPLE 6

The test procedures described above were utilized to evaluate the alkyl/PPO amidotriamine compounds AL-9201 ($C_8$), AL-12223 ($C_{10}$), AL-12246 ($C_{12}$) and AL-12231 ($C_{14}$) in water and FID 84509 at a concentration of 0.0005 w/v %. The results are presented in Table 10, below:

TABLE 10

Disinfection Efficacy of Compounds at 0.0005% in Water and FID 84509

| | | Log$_{10}$ Reduction of Survivors | | | | | | | | | |
|---|---|---|---|---|---|---|---|---|---|---|---|
| | | Water Vehicle | | | | | FID 84509 Vehicle | | | | |
| Microorganism | Time (hrs) | AL9201 | AL12223 | AL12231 | AL12246 | POLYQUAD® | AL9201 | AL12223 | AL12231 | AL12246 | POLYQUAD® |
| C. albicans | 6 | 1.3 | 2.0 | 4.0 | 3.0 | 4.4 | 0.0 | 0.2 | 1.2 | 1.0 | 0.3 |
| | 24 | 2.8 | 2.8 | 3.4 | 3.5 | 5.3 | 0.3 | 0.8 | 2.5 | 2.0 | 0.5 |
| S. marcescens | 6 | 1.1 | 5.3 | <u>6.3</u>$^a$ | <u>6.3</u> | 3.9 | 0.4 | 1.7 | 3.7 | 4.5 | 3.3 |
| | 24 | 1.3 | 5.6 | <u>6.3</u> | 6.3 | <u>6.3</u> | 0.6 | 2.7 | 4.1 | 5.6 | 5.6 |
| S. aureus | 6 | 2.2 | 4.4 | <u>6.3</u> | 5.1 | 3.8 | 0.0 | 1.1 | 4.2 | 5.3 | 2.6 |
| | 24 | 4.6 | 4.0 | <u>6.3</u> | 5.6 | 5.6 | 1.4 | 4.3 | 4.5 | <u>6.3</u> | 3.7 |

$^a$Underlined number indicates no survivors

The results demonstrate that there is a relationship between antimicrobial activity and the size of the alkyl end group, R. As the end group increases in size from C8 to C14, there is a corresponding increase in antimicrobial activity.

EXAMPLE 7

The test procedures described above were utilized to evaluate the alkyl/PPO amidotriamine compounds AL-9201, AL-12223 and AL-12246 in FID 84509 at concentrations of 10, 25, and 50 PPM. The results are presented in Table 11, below:

TABLE 11

Disinfection Activity of Amidotriamine Compounds in FID 84509

| | | Log$^{10}$ Reduction of Survivors | | | | | | | | |
|---|---|---|---|---|---|---|---|---|---|---|
| | Time | AL9201 (C$_8$)$^a$ | | | AL12223 (C$_{10}$) | | | AL12246 (C$_{12}$) | | |
| Microorganism | (hrs) | 0.001% | 0.0025% | 0.005% | 0.001% | 0.0025% | 0.005% | 0.001% | 0.0025% | 0.005% |
| C. albicans | 6 | 0.0 | 0.0 | 0.1 | 0.1 | 1.2 | 3.0 | 0.9 | 2.3 | 3.0 |
| | 24 | 0.2 | 0.3 | 0.3 | 0.5 | 2.0 | 4.1 | 1.2 | 3.4 | 5.2 |
| S. marcescens | 6 | 2.9 | 2.9 | 3.5 | 3.0 | 2.6 | 5.4 | 2.5 | 3.4 | 2.9 |
| | 24 | 4.0 | 3.6 | 4.2 | 4.1 | 5.4 | 6.1$^b$ | 3.9 | 4.4 | <u>6.1</u> |
| S. aureus | 6 | 0.8 | 2.1 | 3.2 | 3.4 | 3.5 | 4.1 | 3.8 | 3.7 | 4.4 |
| | 24 | 3.2 | 3.3 | 3.4 | 3.0 | 4.0 | 5.4 | 4.1 | 3.7 | 4.9 |

$^a$Alkyl chain length
$^b$Underlined number indicates no survivors (<10 cfu/ml) recovered

We claim:
1. A compound of the formula:

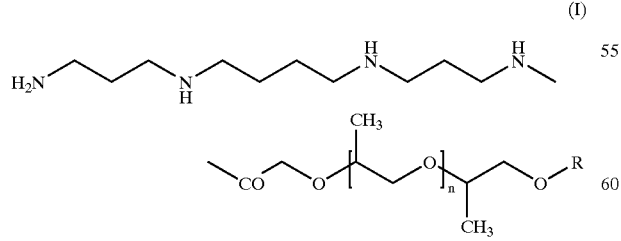

(I)

wherein:
R is C$_6$ to C$_{18}$ alkyl; and
n is 1 to 100; or a pharmaceutically acceptable salt thereof.

2. A compound according to claim 1, wherein R is $C_{12}$ to $C_{16}$ alkyl and n is 6 to 12.

3. A pharmaceutical composition containing a compound of claim 1 in an amount effective to preserve the composition from microbial contamination.

4. A composition for disinfecting contact lenses, comprising a compound of claim 1 in an amount effective to disinfect contact lenses, and a pharmaceutically acceptable vehicle therefor.

\* \* \* \* \*